US00RE48388E

(19) United States
(12) Reissued Patent
Pedicini

(10) Patent Number: US RE48,388 E
(45) Date of Reissued Patent: *Jan. 12, 2021

(54) ELECTRIC MOTOR DRIVEN TOOL FOR ORTHOPEDIC IMPACTING

(71) Applicant: DePuy Synthes Products, Inc., Raynham, MA (US)

(72) Inventor: Christopher Pedicini, Nashville, TN (US)

(73) Assignee: DePuy Synthes Products, Inc., Raynham, MA (US)

( * ) Notice: This patent is subject to a terminal disclaimer.

(21) Appl. No.: 15/098,662

(22) Filed: Apr. 14, 2016

Related U.S. Patent Documents

Reissue of:
(64) Patent No.: 8,695,726
Issued: Apr. 15, 2014
Appl. No.: 12/980,329
Filed: Dec. 29, 2010

(51) Int. Cl.
*B25D 17/00* (2006.01)
*A61B 17/16* (2006.01)
(Continued)

(52) U.S. Cl.
CPC ..... *A61B 17/1628* (2013.01); *A61B 17/1604* (2013.01); *A61B 17/1626* (2013.01);
(Continued)

(58) Field of Classification Search
CPC . A61B 17/1628; A61B 17/92; A61B 17/1659; A61B 17/1604; A61B 17/1626;
(Continued)

(56) References Cited

U.S. PATENT DOCUMENTS 974,267 A * 11/1910 Hennessey et al. . B25D 11/125 173/201
1,920,765 A 8/1933 Ludvik
(Continued)

FOREIGN PATENT DOCUMENTS

DE 103 19 350 A1 11/2004
EP 0 617 926 B1 8/1998
(Continued)

OTHER PUBLICATIONS

Office Action dated May 24, 2016 in Japanese Patent Application No. 2013-547652, along with its English translation.
(Continued)

*Primary Examiner* — Catherine S Williams

(57) ABSTRACT

An orthopedic impacting tool comprises a motor, a linear motion converter, an air chamber, a compression piston, an impacting element, an anvil element, and a broach adapter. The compression piston may cause the impacting element to apply controlled force on a broach adapter to create a precise opening for subsequently disposing a prosthesis in a patient. The tool may further comprise a detent for holding the impacting element in a position until a sufficient pressure is applied to release the impacting element. The tool allows forward or backward impacting for expanding the size or volume of the opening or for facilitating removal of the broach and tool from the opening. A force adjustment control of the tool allows a user to increase or decrease the impact force. A light source and hand grips improve ease of operation of the tool.

17 Claims, 6 Drawing Sheets

(51) Int. Cl.
*A61B 17/92* (2006.01)
*A61B 90/30* (2016.01)

(52) U.S. Cl.
CPC ..... *A61B 17/1659* (2013.01); *A61B 17/92* (2013.01); *A61B 17/1668* (2013.01); *A61B 2017/922* (2013.01); *A61B 2090/309* (2016.02)

(58) Field of Classification Search
CPC ..... A61B 2090/309; A61B 2017/922; A61B 17/1668
See application file for complete search history.

(56) References Cited

U.S. PATENT DOCUMENTS

| | | | | |
|---|---|---|---|---|
| 3,712,390 | A | 1/1973 | Berg | |
| 4,143,585 | A | 3/1979 | Selsam | |
| 4,298,074 | A | 11/1981 | Mattchen | |
| 4,442,906 | A | 4/1984 | Simpson | |
| 5,057,112 | A * | 10/1991 | Sherman et al. | A61B 17/1604 606/100 |
| 5,108,400 | A * | 4/1992 | Appel et al. | A61B 17/1659 173/91 |
| 5,145,369 | A | 9/1992 | Lustig et al. | |
| 5,163,519 | A | 11/1992 | Mead et al. | |
| 5,167,043 | A | 12/1992 | Lopez et al. | |
| 5,352,230 | A | 10/1994 | Hood | |
| 5,485,887 | A * | 1/1996 | Mandanis | A61B 17/92 173/135 |
| 5,553,675 | A | 9/1996 | Pitzen et al. | |
| 5,601,149 | A | 2/1997 | Kawasaki et al. | |
| 5,975,217 | A | 11/1999 | Frenzel et al. | |
| 5,980,528 | A | 11/1999 | Salys | |
| 5,984,027 | A | 11/1999 | Kato | |
| 6,112,830 | A | 9/2000 | Ziegler et al. | |
| 6,264,660 | B1 | 7/2001 | Schmidt et al. | |
| 6,413,230 | B1 | 7/2002 | Haupt et al. | |
| 6,520,266 | B2 * | 2/2003 | Bongers-Ambrosius et al. | B25D 11/12 173/115 |
| 6,644,418 | B2 * | 11/2003 | Haga | 173/48 |
| 6,899,715 | B1 | 5/2005 | Beaty et al. | |
| 6,938,705 | B2 * | 9/2005 | Kikuchi | 173/201 |
| 7,001,393 | B2 | 2/2006 | Schwenke et al. | |
| 7,189,241 | B2 | 3/2007 | Yoon et al. | |
| 7,318,485 | B2 * | 1/2008 | Greese et al. | 173/1 |
| 7,383,895 | B2 * | 6/2008 | Aoki | 173/201 |
| 7,569,057 | B2 | 8/2009 | Liu et al. | |
| 7,708,083 | B2 | 5/2010 | Dresig et al. | |
| 7,708,739 | B2 | 5/2010 | Kilburn et al. | |
| 7,784,562 | B2 * | 8/2010 | Ikuta | 173/201 |
| 7,861,799 | B2 * | 1/2011 | Iwakami et al. | 173/201 |
| 7,926,584 | B2 * | 4/2011 | John et al. | 173/1 |
| 8,069,929 | B2 * | 12/2011 | Sugimoto et al. | 173/128 |
| 8,292,909 | B1 | 10/2012 | DuBois et al. | |
| 8,393,409 | B2 * | 3/2013 | Pedicini | 173/201 |
| 8,465,491 | B2 | 6/2013 | Yedlicka et al. | |
| 8,602,124 | B2 | 12/2013 | Pedicini | |
| 8,636,647 | B2 | 1/2014 | Silvestrini et al. | |
| 8,926,625 | B2 | 1/2015 | Lebet | |
| 8,936,105 | B2 | 1/2015 | Pedicini | |
| 8,936,106 | B2 | 1/2015 | Pedicini | |
| 8,936,603 | B2 | 1/2015 | Mani et al. | |
| 8,936,604 | B2 | 1/2015 | Mani et al. | |
| 8,968,326 | B2 | 3/2015 | Mani et al. | |
| 9,901,354 | B2 | 2/2018 | Pedicini | |
| RE46,954 | E | 7/2018 | Pedicini | |
| RE46,979 | E | 8/2018 | Pedicini | |
| 10,420,567 | B2 | 9/2019 | Pedicini | |
| RE47,963 | E | 4/2020 | Pedicini | |
| RE47,997 | E | 5/2020 | Pedicini | |
| 2005/0057112 | A1 | 3/2005 | Lopatinsky et al. | |
| 2005/0096661 | A1 | 5/2005 | Farrow et al. | |
| 2005/0108400 | A1 | 5/2005 | Kujawski | |
| 2005/0116673 | A1 | 6/2005 | Carl et al. | |
| 2005/0154431 | A1 | 7/2005 | Quistgaard et al. | |
| 2005/0247462 | A1 | 11/2005 | Meixner et al. | |
| 2006/0180631 | A1 | 8/2006 | Pedicini et al. | |
| 2006/0254785 | A1 | 11/2006 | Watanabe | |
| 2007/0085496 | A1 | 4/2007 | Philipp et al. | |
| 2007/0264485 | A1 | 11/2007 | Stepanian et al. | |
| 2008/0181794 | A1 * | 7/2008 | Steinfels | F04B 35/04 417/234 |
| 2008/0215056 | A1 | 9/2008 | Miller et al. | |
| 2008/0234711 | A1 | 9/2008 | Houser et al. | |
| 2011/0118779 | A1 | 5/2011 | Olien et al. | |
| 2011/0307060 | A1 | 12/2011 | Lozier et al. | |
| 2012/0041557 | A1 | 2/2012 | Frigg | |
| 2013/0261681 | A1 | 10/2013 | Bittenson | |
| 2015/0127013 | A1 | 5/2015 | Mani et al. | |
| 2015/0182233 | A1 | 7/2015 | Van Wyk et al. | |
| 2015/0289886 | A1 | 10/2015 | Kfir | |
| 2019/0223889 | A1 | 7/2019 | Pedicini | |

FOREIGN PATENT DOCUMENTS

| | | | |
|---|---|---|---|
| EP | 1754575 | A2 | 2/2007 |
| EP | 2 455 006 | A2 | 5/2012 |
| JP | 60263678 | A | 12/1985 |
| JP | 61-219583 | | 9/1986 |
| JP | 61219583 | A | 9/1986 |
| JP | 6-283217 | | 10/1994 |
| JP | 7-226230 | | 8/1995 |
| JP | 2004299036 | A | 10/2004 |
| JP | 2006-218228 | | 8/2006 |
| WO | WO-9522934 | A1 | 8/1995 |
| WO | WO-0016948 | A1 | 3/2000 |
| WO | WO-2004079214 | A1 | 9/2004 |
| WO | 2010/045158 | A2 | 4/2010 |

OTHER PUBLICATIONS

International Search Report and Written Opinion dated Nov. 2, 2016 in International Application No. PCT/US2016/015380.
International Search Report and Written Opinion issued in PCT Application No. PCT/US2013/029944 dated Jul. 18, 2013.
Canadian Search Results in CA Application No. 2,823,207 on Jun. 16, 2017.
Extended European Search Report for EP App. No. 16193018.5 dated Mar. 30, 2017.
Extended European Search Report for EP App. No. 17199731.5 dated Feb. 13, 2018.
International Preliminary Report on Patentability issued in PCT Application No. PCT/US2011/067626 dated Jul. 2, 2013.
International Search Report and Written Opinion issued in PCT Application No. PCT/US2011/067626 dated Jun. 29, 2012.
Non-Final Office Action issued in U.S. Appl. No. 14/250,102 dated May 11, 2017.
Japanese Office Action issued in JP Application No. 2013-547652 dated Sep. 9, 2015 (english translation included).
Japanese Office Action issued in JP Application No. 2016-210624 dated Aug. 18, 2017 (english translation included).
Japanese Office Action issued in JP Application No. 2017-195035 dated Jul. 8, 2018 (english translation included).
Non-Final Office Action issued in U.S. Appl. No. 12/980,329 dated Jun. 10, 2013.
Canadian Office Action for CA Application No. 2,872,182 dated Apr. 8, 2019.
Japanese Office Action issued in JP Application No. 2018-153615 dated Aug. 20, 2019 (english translation included).
Extended European Search Report for EP App. No. 19150701.1 dated Oct. 21, 2019.
European search report received for European Patent Application No. 11854028.5, dated Oct. 29, 2014.

* cited by examiner

ELECTRIC MOTOR DRIVEN TOOL FOR ORTHOPEDIC IMPACTING

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS REFERENCE TO RELATED APPLICATIONS

The present application *is a reissue of U.S. Pat. No. 8,695,726 issued Apr. 15, 2014 which* claims priority under 35 U.S.C. [§119] *§ 119* on the U.S. provisional patent application Ser. No. 61/290,336, filed on Dec. 28, 2009, the disclosure of which is incorporated by reference.

FIELD

The present disclosure relates to electric tools for impacting in orthopedic applications, and, more particularly, to an electric motor driven tool for orthopedic impacting that is capable of providing controlled impacts to a broach, chisel, or other device for creating an opening in an area (in a bone structure, for example) to securely receive prosthesis within the area.

In the field of orthopedics, prosthetic devices such as artificial joints, are often implanted or seated in a patient's body by seating the prosthetic device in a cavity of a bone of the patient. The cavity must be created before the prosthesis is seated or implanted, and traditionally, a physician may remove worn, excess, or diseased bone structure from the area in which the cavity will be formed, and then drill and hollow out a cavity along the medullar canal of the bone. A prosthesis usually includes a stem or other protrusion that serves as the particular portion of the prosthesis that is inserted into the cavity.

To create such a cavity, a physician may use a broach, which broach conforms to the shape of the stem of the prosthesis. Solutions known in the art include providing a handle with the broach, which handle the physician may grasp while hammering the broach into the implant area. Unfortunately, this approach is clumsy and unpredictable as being subject to the skill of the particular physician. This approach almost will always inevitably result in inaccuracies in the location and configuration of the cavity. Further, this approach carries with it the risk that the physician will damage bone structure in unintended areas.

Another technique for creating the prosthetic cavity is to drive the broach pneumatically, that is, by compressed air. This approach is disadvantageous in that it prevents portability of an impacting tool, for instance, because of the presence of a tethering air line, air being exhausted from a tool into the sterile operating field and fatigue of the physician operating the tool. Further this approach, as exemplified in U.S. Pat. No. 5,057,112 does not allow for precise control of the impact force or frequency and instead functions very much like a jackhammer when actuated. Again, this lack of any measure of precise control makes accurate broaching of the cavity more difficult.

Another disadvantage of tools known in the art is the accumulation of fluids, such as body fluids or moisture, on handgrips of such tools during prolonged periods of use. For example, difficulty of operation of a broach impacting device known in the art may increase during a surgical procedure as handgrips may become saturated with bodily fluids and thus the physician's hold on such a prior art device may become impaired.

Consequently, there exists a need for an impacting tool that overcomes the various disadvantages in the prior art.

In view of the foregoing disadvantages of the prior art, an electric motor-driven orthopedic impacting tool configured to include all the advantages of the prior art, and to overcome the drawbacks inherent therein is provided. The tool may be used by orthopedic surgeons for orthopedic impacting in for example hips, knees, and shoulders. The tool is capable of holding a broach, chisel, or other device and gently tapping the broach, chisel or other device into the cavity with controlled percussive impacts, resulting in a better fit for the prosthesis or the implant. Further, the control afforded by such an electrically manipulated broach, chisel, or other device allows adjustment of the impact settings according to a particular bone type or other profile of a patient. The tool additionally enables proper seating or removal of the prosthesis or the implant into or out of an implant cavity.

In an embodiment, an electric motor-driven orthopedic impacting tool comprises a control unit, a housing, a linear motion converter, at least one reducing gear, an impacting element (also referred to herein as a striker), an air chamber, a compression piston, and a force adjustment control means (hereinafter referred to as 'control means'). The tool may further include a motor, an LED, a handle portion with at least one handgrip for comfortable gripping the tool, a broach adapter, a battery, a feedback system and a nosepiece for the broach adapter. At least some of the various components are preferably contained within the housing. The tool is capable of applying cyclic impact forces on a broach, chisel, or other device, or an implant and of finely tuning impact force to a plurality of levels of impact force.

In an embodiment, the tool further comprises a control means, which means includes a force adjustment element, and which element may control the impact force and avoid damage caused by uncontrolled impacts. The force may be regulated electronically or through the use of mechanical detents. The mechanical detent allows for an increased impact force without sacrificing control or precision of the broach machining operation.

The tool further comprises an anvil element, which anvil element includes both a forward and rearward point of impact and a guide that constrains the striker to move in a substantially axial direction. In operation, the movement of the striker along the guide of the anvil element continues in either a forward or rearward direction until the striker hits the point of impact. As used in this context, "forward direction" connotes movement of the striker toward a broach or patient, and "rearward direction" connotes movement of the striker away from the broach or chisel or patient. If the impact point is at the front of the tool, i.e., in a forward direction, the impact causes the percussive three to be transmitted to a broach or chisel, pushing it further into the cavity. If the impact point is at the rear of the tool, the percussive force tends to pull the broach or chisel out of the cavity. The selectivity of either bidirectional or unidirectional impacting provides flexibility to a surgeon in either cutting or compressing material within the implant cavity, in that the choice of material removal or material compaction is often a critical decision in a surgical procedure. The impact point may be in the form of an plate that is disposed at an end or each end of the anvil element.

The tool is further capable of regulating the frequency of the striker. By regulating the frequency of the striker, the tool may impart a greater total time-weighted percussive impact, while maintaining the same impact magnitude. This allows for the surgeon to control the cutting speed of the broach or chisel. For example, the surgeon may choose cutting at a faster rate (higher frequency impacting) during the bulk of the broach or chisel movement and then slow the cutting rate as the broach or chisel approaches a desired depth.

A user may firmly hold the tool by the handle portion and utilize light emitted by the LED to light up a work area and accurately position the broach, chisel, or other device on a desired location on the prosthesis or the implant. The reciprocating movement imparted on broach, chisel, or other device causes tapping of the implant and/or broach, chisel, or other device and thereby enables proper seating or removal of a prosthesis or implant into or out of an implant cavity, or controlled impacting of a broach, chisel, or other device to create or shape an implant cavity. The tool may also include a feedback system that warns the surgeon, when a bending or off-line orientation beyond a certain magnitude is detected at a broach, chisel, or other device/implant interface.

These together with other aspects of the present disclosure, along with the various features of novelty that characterize the present disclosure, is pointed out with particularity in the claims annexed hereto and forms a part of this present disclosure. For a better understanding of the present disclosure, its operating advantages, and the specific objects attained by its uses, reference should be made to the accompanying drawing and descriptive matter in which there are illustrated exemplary embodiments of the present disclosure.

BRIEF DESCRIPTION OF THE DRAWINGS

The advantages and features of the present invention will become better understood with reference to the following detailed description and claims taken in conjunction with the accompanying drawings, wherein like elements are identified with like symbols, and in which::

Like references numerals refer to like parts throughout the description of several views of the drawings.

LIST OF ELEMENTS IN FIGURES

1 Broach Adapter
2 Anvil antirotation element
3
4 Striker
5 Forward Air Chamber
6 Compression Piston
7 Gear Reducer
8 Motor
9 Gear Reducer
10 Detent
11 Forward Striker Air Chamber
12 Linear Motion Converter
13 Broach Quick connect
14 Anvil
15 Forward anvil impact plate
16 Rear anvil impact plate
17 Rear air Chamber
18
19 Air Passageway

DETAILED DESCRIPTION OF THE DISCLOSURE

The best mode for carrying out the present disclosure is presented in terms of its preferred embodiment, herein depicted in the accompanying figures. The preferred embodiments described herein detail for illustrative purposes are subject to many variations. It is understood that various omissions and substitutions of equivalents are contemplated as circumstances may suggest or render expedient, but are intended to cover the application or implementation without departing from the spirit or scope of the present disclosure.

The terms "a" and "an" herein do not denote a limitation of quantity, but rather denote the presence of at least one of the referenced items.

Referring now to FIGS. 1-6, the present disclosure provides an electric motor-driven orthopedic impacting tool with controlled percussive impacts. The tool includes the capability to perform single or multiple impacts as well as impacting of variable speeds, forces and frequencies. The impact force can be tuned to one of a variety of levels by setting the impact force either electronically or through the use of detents. The detent facilitates the generation of a sufficient strike force to make a meaningful impact in the broach, chisel, or other device, or surgical area.

The tool includes a housing. The housing securely covers and holds a plurality of components of the tool. In an embodiment, the housing contains a motor, at least one reducing gear, a linear motion converter, a compression chamber, an impacting element (alternately referred to as a striker), a force or impact adjustment control means (hereinafter referred to as 'control means'), and an anvil element with a forward impact plate and a rearward impact plate (which impact plates may be part of the anvil, for example).

The tool further may include a handle portion with at least one hand grip for comfortable and secure holding of the tool while in use, a broach adapter, a battery, and a positional sensor, a directional sensor, and/or a torsion sensor. The tool may further comprise an lighting element such as an LED to provide light in the work area in which a user employs the tool. The broach adapter can be coupled to an anvil, of the anvil element for example, through a quick connect mechanism at the end of the tool that is directed at a patient when the tool is in use.

Figure 1:
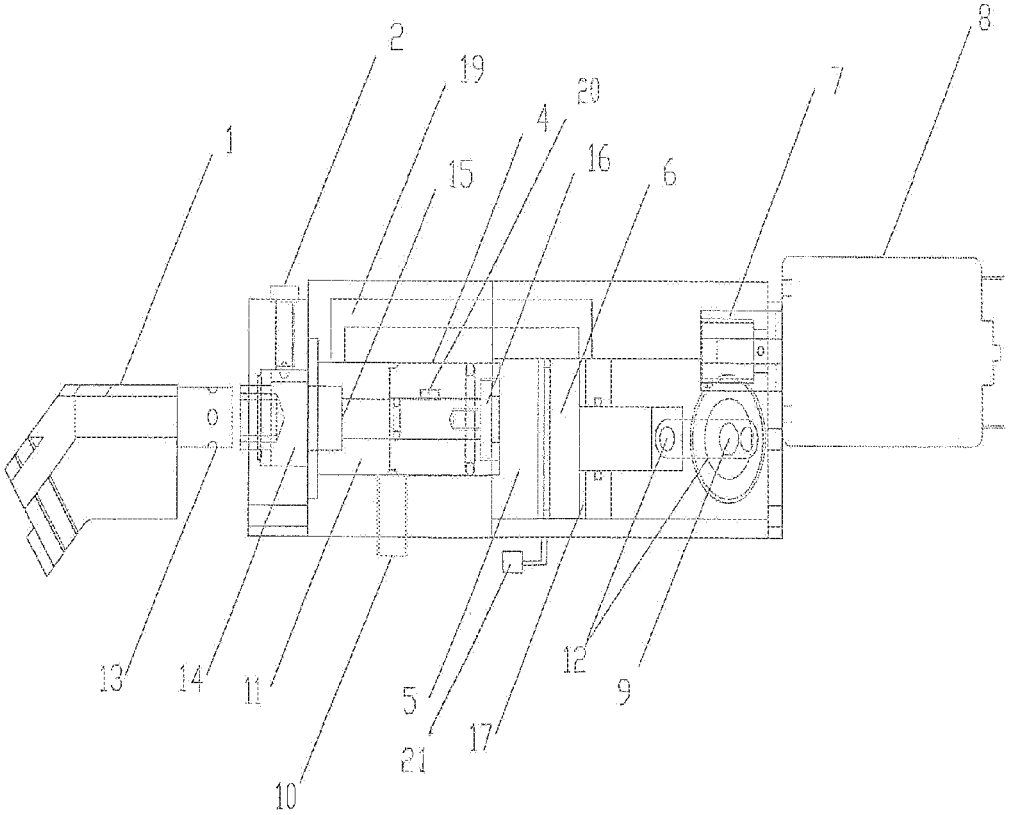
FIG. 1 shows a perspective view of an orthopedic impacting tool, in accordance with an exemplary embodiment of the present disclosure.
Figure 2:
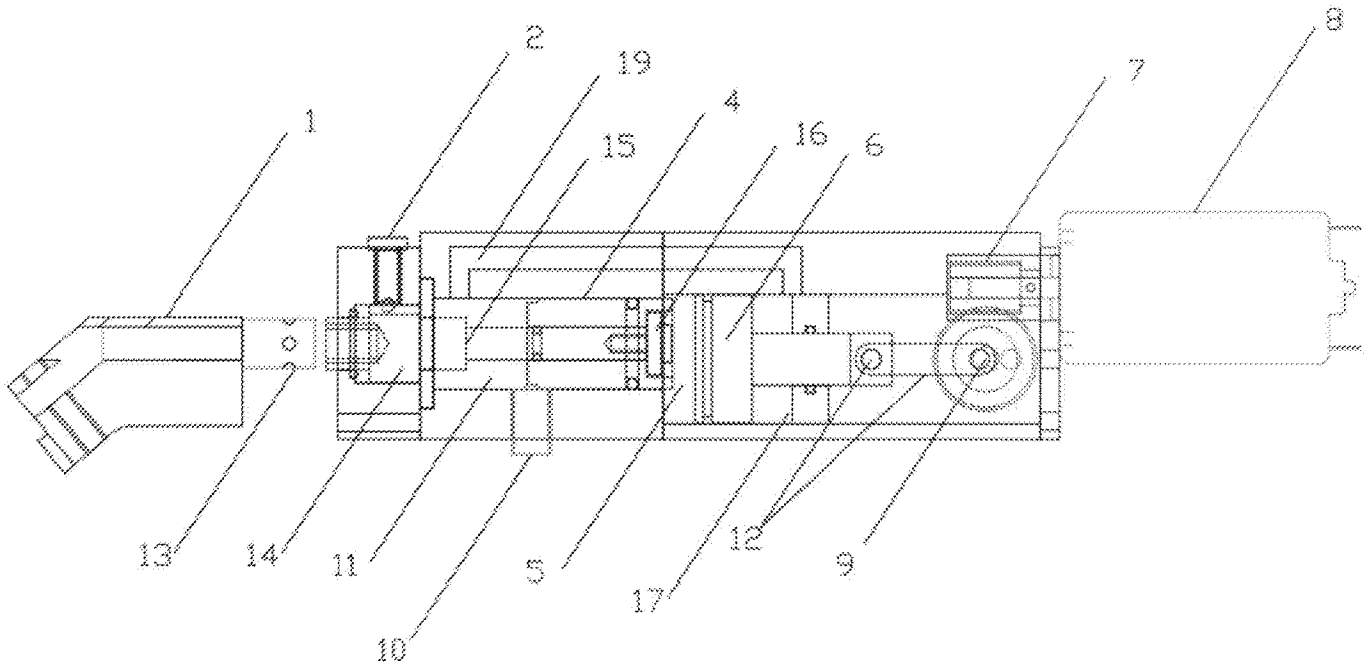
FIG. 2 shows a perspective view of a compression piston compressing air against a striker of an orthopedic impacting tool, in accordance with an exemplary embodiment of the present disclosure.
Figure 3:
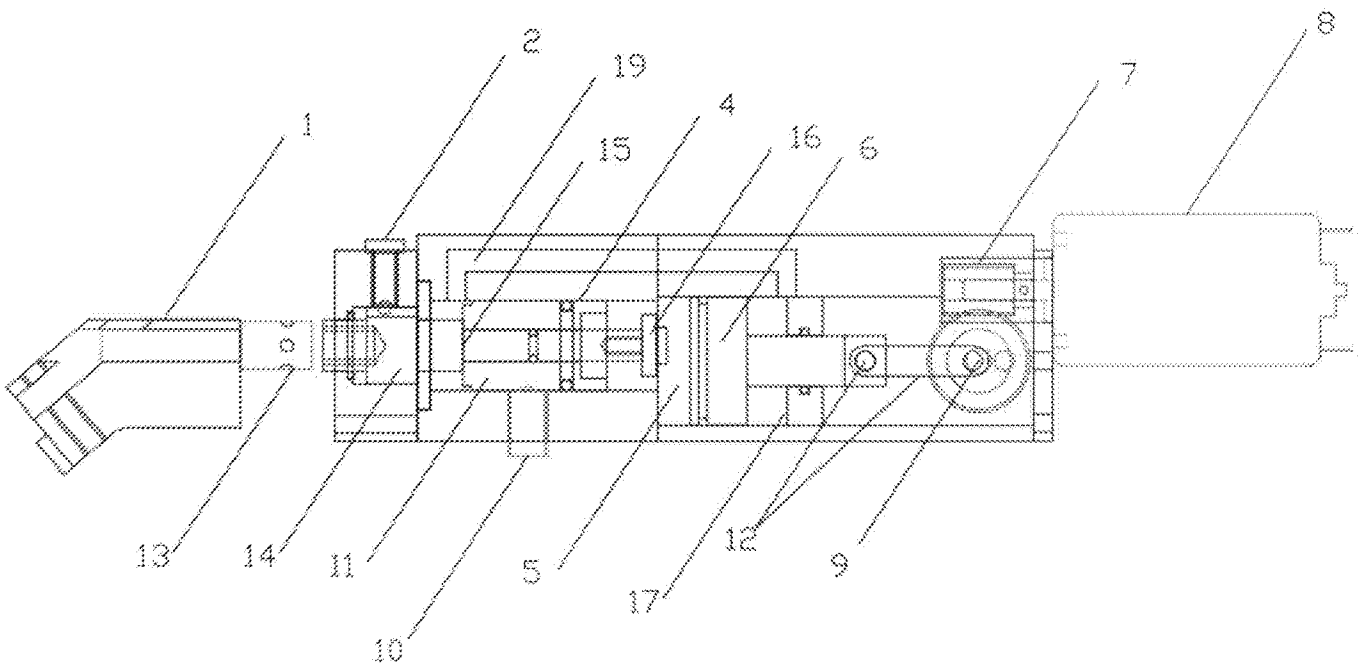
FIG. 3 shows a striker releasing and striking an anvil element, in accordance with an exemplary embodiment of the present disclosure.
Figure 4:
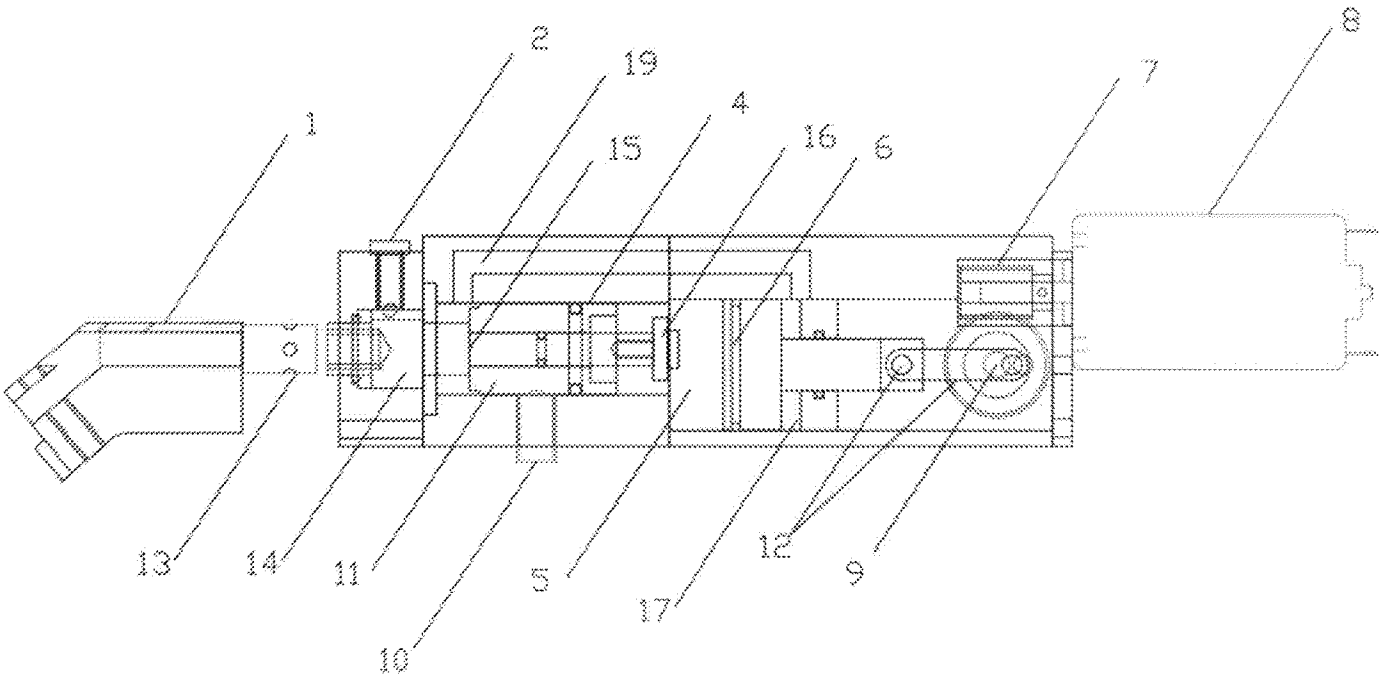
FIG. 4 shows a compression piston of an orthopedic impacting tool returning from a forward position and compressing air on the forward side of a striker, in accordance with an exemplary embodiment of the present disclosure.
Figure 5:
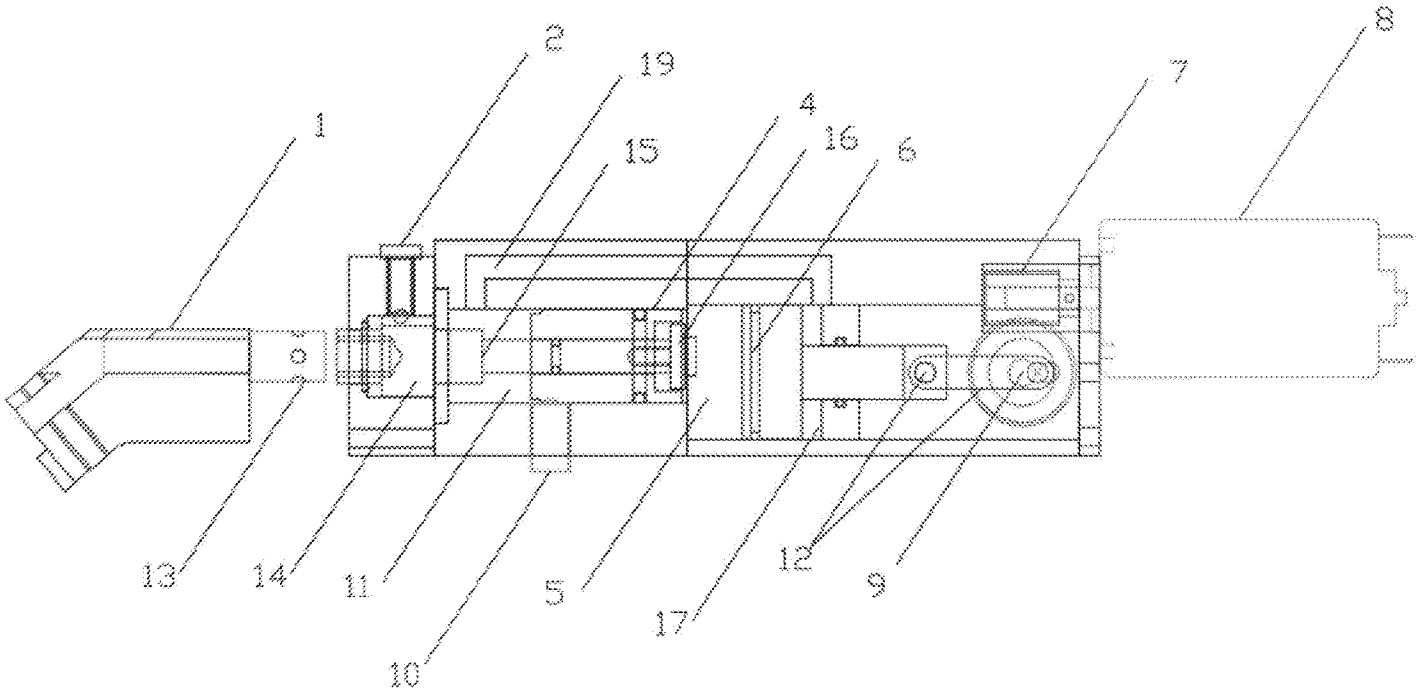
FIG. 5 shows a striker of an orthopedic impacting tool moving rearward, in accordance with an exemplary embodiment of the present disclosure.
Figure 6:
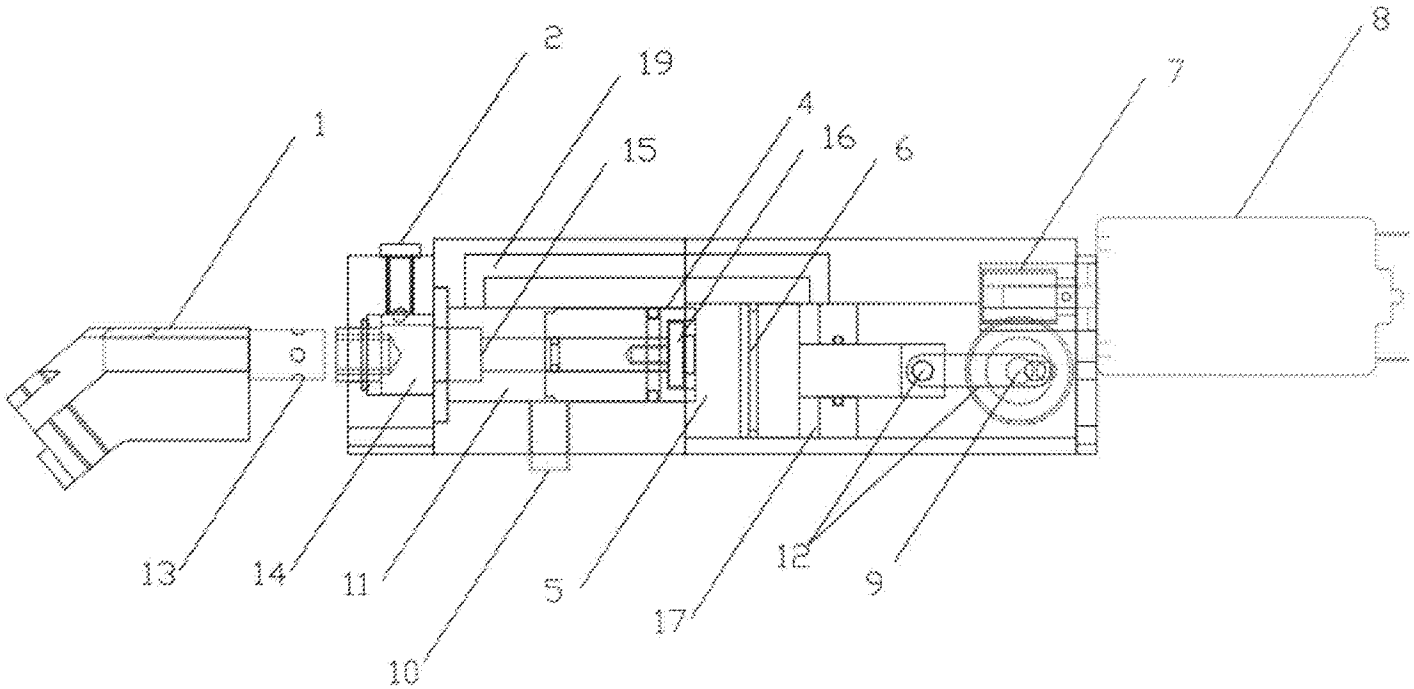
FIG. 6 shows a striker of an orthopedic impacting tool impacting a rear anvil impact plate, in accordance with an exemplary embodiment of the present disclosure.

In an embodiment, and referring now to FIG. 1, the linear motion converter comprises a slider crank mechanism 12, which slider crank is operatively coupled to the motor 8 and reducing gears 7 and 9. The tool further comprises an air chamber 5, 17 that accepts a compression piston 6 with a first end and a second end, which compression piston 6 is actuated by the linear motion converter 12. As the compression piston will have a smaller longitudinal dimension than the air chamber that contains the piston, it will be apparent that an air mass will be present at either end of the compression piston while the compression piston is within the air chamber. Hereinafter, the air mass disposed between the head of compression piston and the striker will be referred to as the "forward air chamber portion" or "forward air chamber," 5 and the air mass disposed between the end of the compression piston that is proximate to the linear motion converter and the motor of the tool will be referred to as the "rear air chamber portion" or "rear air chamber" 17.

In an embodiment of the present disclosure the motor of the tool causes the linear motion converter to move the compression piston until sufficient pressure is built within the forward air chamber 5 that is disposed between the forward end of the compression piston and the rearward end of the striker 4 to either overcome a detent 10 that otherwise retains the striker in a rearward position and/or the inertia and frictional force that holds the striker 4 in a position. Once this sufficient pressure is reached, the force of the air pressure accelerates the striker 4, which striker 4 slides axially down a cavity internal to the tool housing and strikes the forward anvil impact plate 15. The resultant force is communicated through the anvil 14 that is proximate to the impact plate 15 and, optionally, through the broach adapter 1 (which adapter will be described in more detail below) to which a broach, chisel, or other device for seating or removing an implant, or prosthesis may be attached.

As the compression piston 6 continues through its stroke it moves towards the rear direction, compressing the air mass in the rear air chamber 17. This air mass may be communicated through an air passageway 19 to the front side of the striker 4, creating a returning force on the striker 4, which returning force causes the striker 4 to move in a rear direction, i.e., a direction away from the point of impact of the striker the forward anvil impact plate 15. The striker continues to move until it impacts the rear anvil impact plate 16. Striking the rear impact plate creates a rear directed force on the anvil 14. In the event that a broach adapter 1 is attached to the anvil 14, the force is communicated through the broach adapter 1 to which the broach, chisel, or other device for seating or removing an implant, or prosthesis is attached. Thus in one complete cycle, a forward and rear directed impacting force can be applied on the broach, chisel, or other device, or implant/prosthesis.

In an embodiment, the compression piston preferably has a cavity on the head thereof, which cavity creates pressure during the return stroke of the piston, which pressure causes the front end of the striker to move away from the forward anvil impact plate impact the rearward point of impact of the anvil element. It will be apparent that the striker impacting the rear anvil impact plate will communicate a negative force to the front of the anvil (and broach, chisel, or other device), which negative force will move the broach, chisel, or other device away from the location of impact in a surgical area.

The slider crank embodiment of the tool facilitates controlled continuous impacting of the striker and anvil. For such continuous impacting, after causing compression by the compression piston, the slider crank returns to the bottom of its stroke, which return releases pressure on the striker and, in the above-described embodiment wherein the piston comprises a cavity on the head thereof, may pressurize the front of the striker, causing the striker to return to its initial rest position.

For a single stroke, the linear motion converter (such as the slider crank described herein) will stop at or near the rear position, thus releasing the forward pressure on the striker and allowing the striker to return it to its starting position in readiness for another stroke. In this operational mode, a user may cause the tool to impact selectively (as opposed to repeatedly), thus allowing further control of the impacts and the creation or shaping of the surgical area, for example.

A positional sensor, coupled operatively to the control unit may be provided to assist in regulating a preferred positional cyclic operation of the linear motion converter. For example, the control unit may cause the slider crank to come to rest at or near the fully back position in readiness to generate pressure for the next impact upon receiving a signal from the positional sensor that the slider crank has reached the bottom dead center position. In another embodiment, the control unit may be directly coupled to the linear motion converter for initiating and ceasing operation of the linear motion converter.

The control unit is further capable of operating the force control means for selectively tuning the amount of impact force per cycle. By controlling the impact force the tool can avoid damage caused by uncontrolled impacts or impacts of excessive force. For example, a user may reduce the impact setting in the case of an elderly patent with osteoporosis, or may increase the impact setting for more resilient or intact athletic bone structures.

One such force control preferably comprises a selectable release setting on a mechanical detent that holds the striker. It will be apparent that the striker will impact the anvil with greater force in the case where the pressure needed to dislodge the striker from the detent is increased. In another embodiment, the detent may comprise a solenoid, which solenoid may activate upon a predetermined buildup of pressure, after which the striker 4 is released, allowing it to impact the anvil.

The control unit may also control the force of impacting by modulating the speed of advancing (forward directional travel) and/or the speed of retraction (rearward directional travel) of the compression piston. It will be apparent that the modulation of speed of the compression piston will affect the buildup of pressure for forward and rearward directional travel of the striker. For example, where the speed of the forward direction of the piston relatively high, and the speed of the rearward direction of the piston is relatively low, the velocity of the striker in the forward direction will be much higher, causing the imparted percussive impact of the striker to be greater in the forward direction of the piston and striker. This modulation of the speed of the piston in the forward and rearward direction allows a user to create a greater impacting force, when so desired (e.g., to create a surgical area) or a greater rearward force, to facilitate removing a broach, chisel, or other device from the surgical area, for example. In the instance where the forward and rear velocities are the same, the tool allows for bidirectional movement of the broach, chisel, or other device during operation, which creates a very efficient technique for machining the cavity.

The motor of the tool may be configured to assist particularly with such multidirectional impacting. In an embodiment, the motor may operate under pulse-width modulation for rearward striking and may operate under full or continuous speed for forward striking of the striker. In such operation, the broach, chisel, or other device attached to the tool may undergo near forward only motion, which operation will facilitate the creation of an implant seat. Alternatively, the motor may operate under pulse-width modulation for forward striking and may operate under full or continuous speed for rearward impacting, which operation can create an extraction motion useful for dislodging a broach, chisel, or other device that has become stuck or removing an implant.

In a further embodiment, the tool comprises a positional sensor, such as an anvil positional sensor that may be operatively coupled to the control unit of the striker of the tool. This positional sensor is capable of determining whether the operator is pushing or pulling on the tool. For instance, the sensor may determine such pushing or pulling based upon the position of the broach-holding adapter or anvil. This determination can have the effect that when a user is exerting force on the tool in a particular direction the impacting of the striker is accordingly adjusted. For example, if the sensor determines that the user is pushing on the tool or is pushing the tool against an object, that sensor can cause the striker to impact in a forward direction. If the sensor determines that the user is pulling on the tool, that sensor may cause the striker to impact in a rearward direction or may cause a pulling force to be exerted on the striker by way of the cycling of the slider crank.

The tool may further comprise a lighting element, and, in an embodiment, the lighting element may comprise an LED arrangement, which lighting element may be capable of illuminating a user's work area. In an embodiment, the LED may be disposed on the housing of the tool and may be oriented toward a patient's body or surgical cavity.

The tool may further comprise a plate or other flat surface at the end of the tool that is distal to the surgical area, which plate may allow a user to apply selective manual pressure on a broach, chisel or other device, or a surgical implant as dictated by surgical or physical conditions. For instance, if a broach is firmly lodged within a cavity such that the operation of the tool would not remove the broach, the user may manually tap on the plate to dislodge the broach.

The tool may further comprise a torsion sensor, which torsion sensor may be capable of determining a lateral or deviating force or movement of the tool, such that if the tool is sensed to deviate from a predetermined magnitude at the broach/implant interface, a signal may emit to notify the user of such deviation. In this manner and otherwise, the tool facilitates consistent axial broaching and implant seating.

In a further embodiment, the broach adapter may comprise a parallel 4-bar arrangement. In this embodiment, the adapter may receive a broach for anterior or posterior joint replacement. The parallel 4-bar mechanism of the adapter may facilitate receiving and orienting the broach in a variety of positions, such as in a centered position, or in an offset left or right position. The adapter will maintain the broach in on orientation that is parallel or co-linear to the body of the tool and the striker. The broach adapter may also comprise clamps, a vice, or any other fastener that may securely hold the broach, chisel, or other device, during operation of the tool.

The tool may further comprise handgrips disposed on the housing of the tool, which handgrips may include a rubberized or other tacky coating removably disposed thereon. Such coating facilitates comfortable operation of the tool and improves the user's hold on the tool for increased control thereof and reduced fatigue during operation of the tool.

In use, a user such as a surgeon firmly holds the tool by the handle grip or grips and utilizes light emitted by the LED to illuminate a work area and accurately position a broach, chisel or other device that has been attached to the tool on a desired location on the prosthesis or implant. The reciprocating movement imparted by the tool upon the broach, chisel or other device causes tapping of the implant and thereby enables proper seating or removal of the prosthesis or the implant into or out of an implant cavity. The warning system may alert the user in the event that a bending moment above a certain magnitude is detected at a broach (or chisel or other device)/implant interface, The tool disclosed herein provides various advantages over the prior art. It facilitates controlled impacting at a surgical site, which minimizes unnecessary damage to a patient's body and which allows precise shaping of a implant or prosthesis seat. The tool also allows the user to modulate the direction and force of impacts, which improves the user's ability to manipulate the tool. The force control adjustment of the impact settings allows a user to set the force of impact according to a particular bone type or other profile of a patient. The tool thereby enables proper seating or removal of the prosthesis or the implant into or out of an implant cavity.

The foregoing descriptions of specific embodiments of the present disclosure have been presented for purposes of illustration and description. They are not intended to be exhaustive or to limit the present disclosure to the precise forms disclosed, and obviously many modifications and variations are possible in light of the above teaching. The exemplary embodiment was chosen and described in order to best explain the principles of the present disclosure and its practical application, to thereby enable others skilled in the art to best utilize the disclosure and various embodiments with various modifications as are suited to the particular use contemplated.

What is claimed is:

[1. An orthopedic impacting tool for striking an object, the tool comprising a motor, a linear motion converter, a compression piston operatively coupled to said linear motion converter, said piston having a first end and a second end, an air chamber, an impacting element, a detent for retaining the impacting element in a position, a control unit, an anvil element with a front face and a rear face, said anvil element adapted to accept a portion of a broach adapter, a broach adapter capable of holding a broach, chisel, reamer, or other surgical implement, said broach adapter operatively coupled to said anvil element and being proximate to said first face of the anvil element and distal to said second face of said anvil element, and a hand grip, wherein said control unit directs said motor to move said linear motion converter and causing said compression piston to move and compress air within said air chamber and wherein when said compressed air exceeds the force of the detent the impacting element moves from a first position to a second position, striking said front or rear face of the anvil element, such that the impact element is capable of imparting a force upon the broach adapter in at least one direction.]

[2. The tool of claim 1, wherein said linear motion converter is a slider crank mechanism.]

[3. The tool of claim 1, wherein a retaining force of said detent is controlled by a solenoid that is operatively coupled to the control unit.]

[4. The tool of claim 1, wherein a force adjustment control is operatively coupled to the control unit, which force adjustment control is capable of at least one of changing the speed at which the compression piston moves within the air chamber and changing the retention force of the detent.]

[5. The tool of claim 1, wherein the tool comprises a positional sensor that is operatively coupled to one of the control unit of the tool or the motor of the tool, which sensor may determine whether the tool is being pushed toward an object or pulled away from an object, which sensor causes said control unit or motor of the tool to direct the impacting element to impart a greater force upon said front face of said anvil element and a lesser force on said rear face of said anvil element upon sensing that the tool is being pushed toward an object, and which sensor causes said control unit or motor of the tool to direct the impacting element to impart a lesser force upon said front face of said anvil element and a greater force on said rear face of said anvil element upon sensing that the tool is being pulled away from an object.]

[6. The tool of claim 1, wherein said tool comprises a torsion sensor, which torsion sensor is capable of determining a lateral movement of the tool and which sensor is capable of signaling such movement.]

*7. A surgical impactor for striking an object with a repeatable, controlled striking force to impel operation of a surgical implement in opposing directions, comprising:*

*a housing;*

*a drive mechanism;*

*a control circuit to actuate the drive mechanism to produce the repeatable controlled striking force;*

*a motor configured to be controlled by the control circuit to drive the drive mechanism; and*

*an adapter to receive a surgical implement to interface the object and a striker operable to impact at least two distinct impact surfaces of the adapter responsive to the repeatable, controlled striking force delivered thereto by the drive mechanism, wherein*

*provision of the repeatable, controlled striking force to a first impact surface of the at least two distinct impact surfaces of the adapter impels the adapter in a first direction,*

*provision of the repeatable, controlled striking force to a second impact surface of the at least two distinct impact surfaces impels the adapter in a direction opposite the first direction;*

*the housing contains therein at least the at least two distinct impact surfaces which are each mounted in a stationary position relative to the housing; and*

*the housing also contains therein at least the motor and the striker.*

*8. The surgical impactor of claim 7, wherein the drive mechanism includes a linear motion converter.*

*9. The surgical impactor of claim 8, wherein the linear motion converter is a slider crank mechanism.*

*10. The surgical impactor of claim 7, further comprising:*

*a detent mechanism to provide a retaining force to the striker.*

*11. The surgical impactor of claim 10, wherein the retaining force is controlled by a solenoid operatively coupled to the control circuit.*

*12. The surgical impactor of claim 10, further comprising:*

*a force adjustment control operatively coupled to the control circuit, the force adjustment control operable to adjust a speed at which a compression piston moves within an air chamber.*

*13. The surgical impactor of claim 10, further comprising:*

*a force adjustment control operatively coupled to the control circuit, the force adjustment control operable to adjust the retention force of the detent.*

*14. A surgical impactor for striking an object with a repeatable, controlled striking force to impel operation of a surgical implement in opposing directions, comprising:*

*a housing;*

*a drive mechanism;*

*a control circuit to actuate the drive mechanism to produce the repeatable controlled striking force;*

*a positional sensor operatively coupled to the control circuit to determine whether the surgical impactor is being pushed toward the object or pulled away from the object; and*

*an adapter to receive a surgical implement to interface the object and a striker operable to impact at least two distinct impact surfaces of the adapter responsive to the repeatable, controlled striking force delivered thereto by the drive mechanism, wherein*

*provision of the repeatable, controlled striking force to a first impact surface of the at least two distinct impact surfaces of the adapter impels the adapter in a first direction,*

*provision of the repeatable, controlled striking force to a second impact surface of the at least two distinct impact surfaces impels the adapter in a direction opposite the first direction;*

*the housing contains therein at least the at least two distinct impact surfaces which are each mounted in a stationary position relative to the housing,*

*the positional sensor causes the control circuit to direct the striker to impart a greater force upon the first impact surface of the at least two distinct impact surfaces of the adapter and a lesser force on the second impact surface of an anvil of the at least two distinct impact surfaces of the adapter upon sensing that the surgical impactor is being pushed toward the object, and*

*the positional sensor causes the control circuit to direct the striker to impart a lesser force upon the first impact surface of the at least two distinct impact surfaces of the adapter upon sensing that the surgical impactor tool is being pulled away from the object.*

*15. The surgical impactor of claim 7, further comprising:*

*a torsion sensor operable to determine a lateral movement of the surgical impactor and to communicate the lateral movement to the control circuit.*

*16. The surgical impactor of claim 7, wherein the adapter is operable to communicate positive force to the surgical implement responsive to the striker impacting the first impact surface, wherein the communication of the positive force causes the surgical implement to move toward the object.*

*17. The surgical impactor of claim 7, wherein the adapter is operable to communicate negative force to the surgical implement responsive to the striker impacting the second*

*impact surface, wherein the communication of the second force causes the surgical implement to move away from the object.*

*18. A surgical impactor, comprising:*

*a housing;*

*a drive mechanism;*

*a motor;*

*a control unit operatively coupled to the motor and to the drive mechanism and configured to control the motor and thereby cause movement of the drive mechanism;*

*an adapter configured to receive a surgical implement configured to strike an object;*

*a striker operatively coupled to the adapter, operatively coupled to the drive mechanism, and configured to, in response to the movement of the drive mechanism, provide a repeatable, controlled striking force to the adapter that includes*

*impact of the striker on a first surface of the adapter, thereby moving the adapter in a first direction, and*

*impact of the striker on a second, different surface of the adapter, thereby moving the adapter in a second direction that is opposite to the first direction;*

*wherein the housing contains therein at least the at least two distinct impact surfaces which are each mounted in a stationary position relative to the housing; and*

*wherein the housing also contains therein at least the motor and the striker.*

*19. The surgical impactor of claim 18, wherein the drive mechanism includes a linear motion converter.*

*20. The surgical impactor of claim 18, wherein the linear motion converter is a slider crank mechanism.*

*21. The surgical impactor of claim 18, wherein the surgical implement includes a broach, a chisel, or a reamer.*

*22. The surgical impactor of claim 18, wherein the first surface of the adapter is a forward surface;*

*the second surface of the adapter is a rearward surface;*

*the surgical impactor further comprises a detent configured to retain the striker in a rearward position; and*

*the movement of the drive mechanism is configured to cause the striker to be released from the detent.*

*23. The surgical impactor of claim 18, wherein the first surface of the adapter is a forward surface;*

*the second surface of the adapter is a rearward surface;*

*the surgical impactor further comprises a positional sensor operatively coupled to the control unit;*

*in response to the positional sensor determining that the surgical impactor is moving toward the object, the control unit is configured to cause the striker to impart a greater force upon the first surface and a lesser force on the second surface; and*

*in response to the positional sensor determining that the surgical impactor is moving away from the object, the control unit is configured to cause the striker to impart a lesser force upon the first surface and a greater force on the second surface.*

* * * * *